United States Patent
Takahashi et al.

(10) Patent No.: US 7,754,894 B2
(45) Date of Patent: Jul. 13, 2010

(54) CRYSTALLINE SULFONAMIDE-CONTAINING INDOLE COMPOUND AND PROCESS FOR PREPARING THE SAME

(75) Inventors: Keiko Takahashi, Tsukuba (JP); Kenji Hayashi, Tsukuba (JP); Taichi Abe, Kamisu (JP); Takao Omae, Ushiku (JP); Takashi Kato, Gifu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 352 days.

(21) Appl. No.: 10/571,279

(22) PCT Filed: Sep. 1, 2004

(86) PCT No.: PCT/JP2004/012649

§ 371 (c)(1),
(2), (4) Date: Dec. 26, 2006

(87) PCT Pub. No.: WO2005/026118

PCT Pub. Date: Mar. 24, 2005

(65) Prior Publication Data

US 2007/0082941 A1 Apr. 12, 2007

(30) Foreign Application Priority Data

Sep. 10, 2003 (JP) ............................. 2003-318953

(51) Int. Cl.
*C07D 209/00* (2006.01)
(52) U.S. Cl. ..................................... 548/483
(58) Field of Classification Search ........................ None
See application file for complete search history.

(56) References Cited

U.S. PATENT DOCUMENTS

| | | | |
|---|---|---|---|
| 6,469,043 B1 * | 10/2002 | Haneda et al. | ............... 514/414 |
| 2002/0128480 A1 | 9/2002 | Haneda et al. | |
| 2003/0215523 A1 | 11/2003 | Ozawa et al. | |
| 2004/0018192 A1 * | 1/2004 | Wakabayashi et al. | ... 424/144.1 |

FOREIGN PATENT DOCUMENTS

| EP | 1 074 542 A1 | 2/2001 |
|---|---|---|
| JP | 9-316053 A | 12/1997 |
| JP | 2000-247949 A | 9/2000 |
| WO | WO 2000050395 * | 2/2000 |
| WO | WO 00/50395 A1 | 8/2000 |
| WO | WO 02/36117 A1 | 5/2002 |

OTHER PUBLICATIONS

Chawla et al., "Challenges in Polymorphism of Pharmaceuticals", CRIPS vol. 5, No. 1, Jan.-Mar. 2004 (**4 pages).*
Newman et al., "Solid-state analysis of the active pharmaceutical ingredient in drug products", DDT vol. 8, No. 19, Oct. 2003, p. 898-905.*
Byrn et al., "Solid-State Chemistry of Drugs", 1999, p. 62-63.*
Brittain, Polymorphism in Pharmaceutical Solids, vol. 95, p. 228-229.*
Brittain et al. "Effects of pharmaceutical processing on drug polymorphs and solvates" in Polymorphism in Pharmaceutical Solids, vol. 95, p. 331-361.*
http://www.expresspharmaonline.com/20031023/edit02.shtml.*
Office Action for JP-2005513843 of Jul. 14, 2009.

* cited by examiner

*Primary Examiner*—Golam M. M. Shameem
*Assistant Examiner*—Sun Jae Y Loewe
(74) *Attorney, Agent, or Firm*—Birch, Stewart, Kolasch & Birch, LLP

(57) ABSTRACT

A crystalline form of N-(3-cyano-4-methyl-1H-indol-7-yl)-3-cyanobenzenesulfonamide having a diffraction peak at a diffraction angle (2θ±0.2°) of 19.1° in a powder X-ray diffraction.

1 Claim, 9 Drawing Sheets

CRYSTALLINE SULFONAMIDE-CONTAINING INDOLE COMPOUND AND PROCESS FOR PREPARING THE SAME

TECHNICAL FIELD

The present invention relates to crystalline sulfonamide-containing indole compound which are useful as antitumor agents with angiogenesis inhibitory action, and to a process for preparing the same.

BACKGROUND ART

Sulfonamide-containing indole compounds are useful as antitumor agents with angiogenesis inhibitory action, and among them, an especially notable antitumor effect is exhibited by N-(3-cyano-4-methyl-1H-indol-7-yl)-3-cyanobenzenesulfonamide (hereinafter referred to as "compound (5b)") (see Patent document 1). A process for preparing the compound (5b) is disclosed in Example 1 of Patent document 1.

[Patent document 1] WO00/50395

DISCLOSURE OF THE INVENTION

Problems to be Solved by the Invention

Upon several test runs of Example 1 of Patent document 1, the present inventors have found that it is not always possible to obtain consistent crystals. The active ingredient of a drug must be stably supplied as a product of consistent quality. Therefore, when the active ingredient of a drug is obtained as a crystalline substance, it preferably consists of a single crystal form and has satisfactory physical properties such as stability against light and other influences. It is also desirable to develop a process for stable production of such crystals on an industrial scale. It is therefore an object of the present invention to provide crystals of the compound (5b) which consist of a single crystal form, and a process for preparing the same.

Means for Solving the Problems

As a result of much avid research, the present inventors have discovered that a single crystal form of the compound (5b) can be obtained by using a specific solvent during crystallization of the compound (5b), and have succeeded in completing this invention.

Specifically, the present invention provides the following [1] to [30].

[1] A crystalline form (Form C) of N-(3-cyano-4-methyl-1H-indol-7-yl)-3-cyanobenzenesulfonamide having a diffraction peak at a diffraction angle (2θ±0.2°) of 11.4° in a powder X-ray diffraction.

[2] A crystalline form (Form C) according to [1] further having a diffraction peak at a diffraction angle (2θ±0.2°) of 19.1° in a powder X-ray diffraction.

[3] A crystalline form (Form C) of N-(3-cyano-4-methyl-1H-indol-7-yl)-3-cyanobenzenesulfonamide having an absorption peak at a wavenumber of 1410±1 $cm^{-1}$ in an infrared absorption spectrum (KBr).

[4] A crystalline form (Form C) according to [3] further having an absorption peak at a wavenumber of 1443±1 $cm^{-1}$ in an infrared absorption spectrum (KBr).

[4-2] A crystalline form (Form C) according to [1] or [2] having an absorption peak at a wavenumber of 1410±1 $cm^{-1}$ in an infrared absorption spectrum (KBr).

[4-3] A crystalline form (Form C) according to [4-2] further having an absorption peak at a wavenumber of 1443±1 $cm^{-1}$ in an infrared absorption spectrum (KBr).

[5] A crystalline form (Form C) of N-(3-cyano-4-methyl-1H-indol-7-yl)-3-cyanobenzenesulfonamide having a peak at a chemical shift of approximately 143.4 ppm in a $^{13}C$ solid state NMR spectrum.

[6] A crystalline form (Form C) according to [5] further having a peak at a chemical shift of approximately 131.1 ppm in a $^{13}C$ solid state NMR spectrum.

[6-2] A crystalline form (Form C) according to any one of [1] to [4-3] having a peak at a chemical shift of approximately 143.4 ppm in a $^{13}C$ solid state NMR spectrum.

[6-3] A crystalline form (Form C) according to [6-2] further having a peak at a chemical shift of approximately 131.1 ppm in a $^{13}C$ solid state NMR spectrum.

[7] A process for preparing a crystalline form (Form C) of N-(3-cyano-4-methyl-1H-indol-7-yl)-3-cyanobenzenesulfonamide according to any one of [1] to [6-3], characterized in that N-(3-cyano-4-methyl-1H-indol-7-yl)-3-cyanobenzenesulfonamide is crystallized using a simple solvent selected from the group consisting of n-propyl alcohol, isopropyl alcohol, n-butyl alcohol, s-butyl alcohol, t-butyl alcohol and water, or a mixed solvent thereof as a crystallization solvent.

[8] A process according to [7], wherein the crystallization solvent is a simple solvent of isopropyl alcohol or s-butyl alcohol, or a mixed solvent of s-butyl alcohol and water or a mixed solvent of isopropyl alcohol and water.

[9] A process according to [7], wherein the crystallization solvent is a mixed solvent of s-butyl alcohol and water (volume ratio=3:1-5:1) or a mixed solvent of isopropyl alcohol and water (volume ratio=9:1-10:1).

[10] A process according to [7], wherein the crystallization solvent is a mixed solvent of s-butyl alcohol and water (volume ratio=3.9:1-4.1:1).

[11] A process according to [7], wherein N-(3-cyano-4-methyl-1H-indol-7-yl)-3-cyanobenzenesulfonamide is heated and dissolved in a solvent and then crystallized.

[12] A process according to [7], wherein N-(3-cyano-4-methyl-1H-indol-7-yl)-3-cyanobenzenesulfonamide is heated and dissolved in a solvent and then crystallized by gradual cooling.

[13] A process for preparing a crystalline form (Form C) of N-(3-cyano-4-methyl-1H-indol-7-yl)-3-cyanobenzenesulfonamide according to any one of [1] to [6-3], characterized in that N-(3-cyano-4-methyl-1H-indol-7-yl)-3-cyanobenzenesulfonamide is heated at 80-130° C.

[14] A process for preparing a crystalline form (Form C) of N-(3-cyano-4-methyl-1H-indol-7-yl)-3-cyanobenzenesulfonamide according to any one of [1] to [6-3], characterized in that N-(3-cyano-4-methyl-1H-indol-7-yl)-3-cyanobenzenesulfonamide is heated and stirred in water at 60-90° C.

[15] A process for preparing a crystalline form (Form C) of N-(3-cyano-4-methyl-1H-indol-7-yl)-3-cyanobenzenesulfonamide according to any one of [1] to [6-3], characterized in that a crystalline form of N-(3-cyano-4-methyl-1H-indol-7-yl)-3-cyanobenzenesulfonamide hydrate are heated at 80-130° C.

[16] A process for preparing a crystalline form (Form C) of N-(3-cyano-4-methyl-1H-indol-7-yl)-3-cyanobenzenesulfonamide according to any one of [1] to [6-3], characterized in that a crystalline form of N-(3-cyano-4-methyl-1H-indol-7-yl)-3-cyanobenzenesulfonamide hydrate are heated and stirred in water at 60-90° C.

[17] A process for preparing a crystalline form (Form C) of N-(3-cyano-4-methyl-1H-indol-7-yl)-3-cyanobenzenesulfonamide according to any one of [1] to [6-3], characterized in that a mixture comprising a crystalline form of N-(3-cyano-4-methyl-1H-indol-7-yl)-3-cyanobenzenesulfonamide anhydrate and a crystalline form of N-(3-cyano-4-methyl-1H-indol-7-yl)-3-cyanobenzenesulfonamide hydrate are heated at 80-130° C.

[18] A process for preparing a crystalline form (Form C) of N-(3-cyano-4-methyl-1H-indol-7-yl)-3-cyanobenzenesulfonamide according to any one of [1] to [6-3], characterized in that a mixture comprising a crystalline form of N-(3-cyano-4-methyl-1H-indol-7-yl)-3-cyanobenzenesulfonamide anhydrate and a crystalline form of N-(3-cyano-4-methyl-1H-indol-7-yl)-3-cyanobenzenesulfonamide hydrate are heated and stirred in water at 60-90° C.

[19] A crystalline form (Form A) of N-(3-cyano-4-methyl-1H-indol-7-yl)-3-cyanobenzenesulfonamide hydrate having a diffraction peak at a diffraction angle (2θ±0.2°) of 8.5° in a powder X-ray diffraction.

[20] A crystalline form (Form A) according to [19] further having a diffraction peak at a diffraction angle (2θ±0.2°) of 25.8° in a powder X-ray diffraction.

[21] A crystalline form (Form A) of N-(3-cyano-4-methyl-1H-indol-7-yl)-3-cyanobenzenesulfonamide hydrate having an absorption peak at a wavenumber of 616±1 cm$^{-1}$ in an infrared absorption spectrum (KBr).

[22] A crystalline form (Form A) according to [21] further having an absorption peak at a wavenumber of 802±1 cm$^{-1}$ in an infrared absorption spectrum (KBr).

[22-2] A crystalline form (Form A) according to [19] or [20] having an absorption peak at a wavenumber of 616±1 cm$^{-1}$ in an infrared absorption spectrum (KBr).

[22-3] A crystalline form (Form A) according to [22-2] further having an absorption peak at a wavenumber of 802±1 cm$^{-1}$ in an infrared absorption spectrum (KBr).

[23] A crystalline form (Form A) of N-(3-cyano-4-methyl-1H-indol-7-yl)-3-cyanobenzenesulfonamide hydrate having a peak at a chemical shift of approximately 134.7 ppm in a $^{13}$C solid state NMR spectrum.

[24] A crystalline form (Form A) according to claim 23 further having a peak at a chemical shift of approximately 126.3 ppm in a $^{13}$C solid state NMR spectrum.

[24-2] A crystalline form (Form A) according to [19] to [22-3] having a peak at a chemical shift of approximately 134.7 ppm in a $^{13}$C solid state NMR spectrum.

[24-3] A crystalline form (Form A) according to [24-2] further having a peak at a chemical shift of approximately 126.3 ppm in a $^{13}$C solid state NMR spectrum.

[25] A pharmaceutical composition comprising a crystalline form according to any one of [1] to [6-3].

[26] An angiogenesis inhibitor comprising a crystalline form according to any one of [1] to [6-3].

[27] An antitumor agent, pancreatic cancer therapeutic agent, colorectal cancer therapeutic agent, gastric cancer therapeutic agent, breast cancer therapeutic agent, prostate cancer therapeutic agent, lung cancer therapeutic agent, ovarian cancer therapeutic agent, cancer metastasis inhibitor, diabetic retinopathy therapeutic agent, rheumatoid arthritis therapeutic agent or angioma therapeutic agent, comprising a crystalline form according to any one of [1] to [6-3].

[28] A method of preventing or treating a disease for which angiogenesis inhibition is effective, comprising administering to a patient, a pharmacologically effective amount of a crystalline form according to any one of [1] to [6-3].

[29] A method of preventing or treating antitumor, pancreatic cancer, colorectal cancer, gastric cancer, breast cancer, prostate cancer, lung cancer, ovarian cancer, cancer metastasis, diabetic retinopathy, rheumatoid arthritis or angioma, comprising administering to a patient, a pharmacologically effective amount of a crystalline form according to any one of [1] to [6-3].

[30] Use of a crystalline form according to any one of [1] to [6-3] for the manufacture of an antitumor agent, pancreatic cancer therapeutic agent, colorectal cancer therapeutic agent, gastric cancer therapeutic agent, breast cancer therapeutic agent, prostate cancer therapeutic agent, lung cancer therapeutic agent, ovarian cancer therapeutic agent, cancer metastasis inhibitor, diabetic retinopathy therapeutic agent, rheumatoid arthritis therapeutic agent or angioma therapeutic agent.

Effect of the Invention

According to the preparing process of the invention, it is possible to easily prepare crystals (Form C) consisting of a single crystal form of the compound (5b) on an industrial scale. The respective crystals (Form A and Form C) of the invention can be prepared as a single crystal form by crystallization or the like and have satisfactory properties including stability to light, rendering them suitable for use as the active ingredient of an antitumor agent. The crystals, Form A are also useful as an intermediate for preparing the crystals, Form C by a thermal transition method.

BEST MODE FOR CARRYING OUT THE INVENTION

Figure 1:
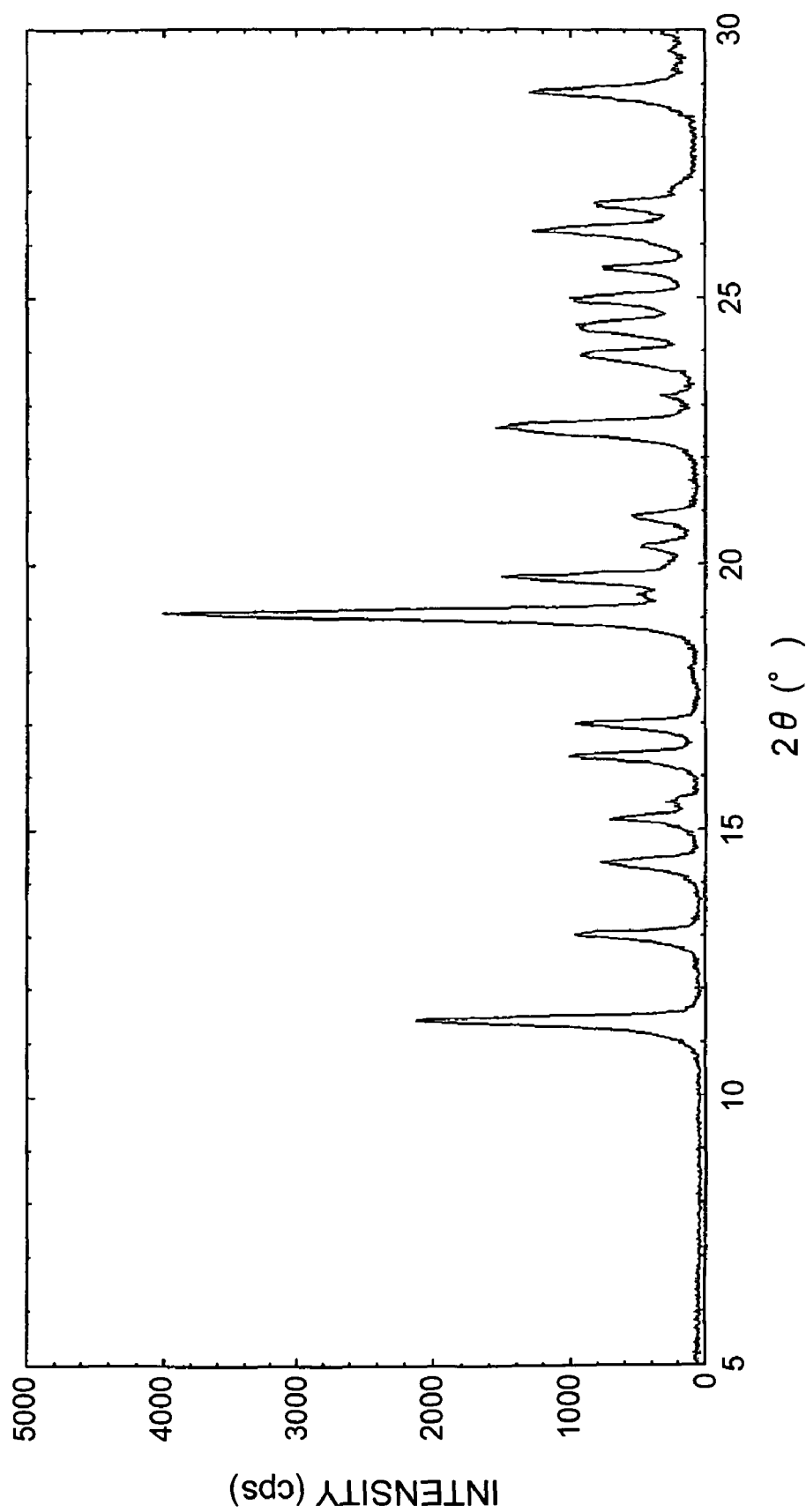
FIG. 1 is a drawing representing a powder X-ray diffraction pattern of the crystals obtained in Example 3A.

The present invention will now be explained in greater detail. The crystals of the invention are crystals (Form A and Form C) of the compound (5b) having the features described below. The measurement conditions for powder X-ray diffraction, infrared absorption spectrum (KBr) and $^{13}$C solid state NMR spectrum are not particularly restricted, but measurement is preferably carried out under the conditions herein described.

A Crystalline Form (Form C) of N-(3-cyano-4-methyl-1H-indol-7-yl)-3-cyanobenzenesulfonamide anhydrate The crystals (Form C) of the invention are anhydrate crystals consisting of a single crystal form of the compound (5b), and they are crystals characterized by having a diffraction peak at a diffraction angle (2θ±0.2°) of 11.4° or crystals characterized by having diffraction peaks at diffraction angles (2θ±0.2°) of 11.4° and 19.1°, in a powder X-ray diffraction. These characteristic peaks in a powder X-ray diffraction are not observed with the crystal obtained by the production process disclosed in Patent document 1 (see Example 1B, Table 6 and FIG. 2 below). The crystals (Form C) of the invention are also crystals characterized by having an absorption peak at a wavenumber of 1410±1 cm$^{-1}$ or crystals having absorption peaks at a wavenumber of 1410±1 cm$^{-1}$ and a wavenumber of 1443±1 cm$^{-1}$, in an infrared absorption spectrum (KBr). Furthermore, the crystals (Form C) of the invention are crystals characterized by having a peak at a chemical shift of approximately 143.4 ppm or crystals characterized by having peaks at chemical shifts of approximately 143.4 ppm and approximately 131.1 ppm, in a $^{13}$C solid-state NMR spectrum.

Since the diffraction angle (2θ) in a powder X-ray diffraction generally has a diffraction angle error in the range of ±0.2°, the aforementioned values for the diffraction angle must be interpreted as including values within a range of ±0.2°. Thus, the present invention encompasses not only crystals whose peak diffraction angle in a powder X-ray diffraction matches exactly, but also crystals whose peak diffraction angle matches with an error of ±0.2°.

Specifically, throughout the present specification, "having a diffraction peak at a diffraction angle (2θ±0.2°) of 11.4°" means "having a diffraction peak at a diffraction angle (2θ) in the range of 11.20°-11.6°", and "having a diffraction peak at a diffraction angle (2θ±0.2°) of 19.1°" means "having a diffraction peak at a diffraction angle (2θ) in the range of 18.9°-19.3°".

Likewise, throughout the present specification, "having an absorption peak at a wavenumber of 1410±1 cm$^{-1}$" means "having an absorption peak at a wavenumber in the range of 1409-1411 cm$^{-1}$", and "having an absorption peak at a wavenumber of 1443±1 cm$^{-1}$" means "having an absorption peak at a wavenumber in the range of 1442-1443 cm$^{-1}$".

Throughout the present specification, "having a peak at a chemical shift of approximately 143.4 ppm" means "having a peak substantially equivalent to a chemical shift of 143.4 ppm, when a $^{13}$C solid state NMR spectrum is measured under ordinary measuring conditions". Also, "having a peak at a chemical shift of approximately 131.1 ppm" as used throughout the present specification likewise means "having a peak substantially equivalent to a chemical shift of 131.1 ppm, when a $^{13}$C solid state NMR spectrum is measured under ordinary measuring conditions".

A Crystalline Form (Form A) of N-(3-cyano-4-methyl-1H-indol-7-yl)-3-cyanobenzenesulfonamide hydrate The crystals (Form A) of the invention are hydrate crystals composed of a single crystal form of the compound (5b), and they are crystals characterized by having a diffraction peak at a diffraction angle (2θ±0.2°) of 8.5° or crystals characterized by having diffraction peaks at diffraction angles (2θ±0.2°) of 8.5° and 25.8°, in a powder X-ray diffraction. The crystals (Form A) of the invention are also crystals characterized by having an absorption peak at a wavenumber of 616±1 cm$^{-1}$ or crystals having absorption peaks at a wavenumber of 616±1 cm$^{-1}$ and a wavenumber of 802±1 cm$^{-1}$, in an infrared absorption spectrum (KBr). Furthermore, the crystals (Form A) of the invention are crystals characterized by having a peak at a chemical shift of approximately 134.7 ppm or crystals characterized by having peaks at chemical shifts of approximately 134.7 ppm and approximately 126.3 ppm, in a $^{13}$C solid state NMR spectrum.

Since the diffraction angle (2θ) in a powder X-ray diffraction generally has a diffraction angle error in the range of ±0.2°, the aforementioned values for the diffraction angle must be interpreted as including values within a range of ±0.2°. Thus, the present invention encompasses not only crystals whose peak diffraction angle in a powder X-ray diffraction matches exactly, but also crystals whose peak diffraction angle matches with an error of ±0.2°.

Throughout the present specification, "having a diffraction peak at a diffraction angle (2θ±0.2°) of 8.5°" means "having a diffraction peak at a diffraction angle (2θ) in the range of 8.3°-8.7°", and "having a diffraction peak at a diffraction angle (2θ±0.2°) of 25.8°" means "having a diffraction peak at a diffraction angle (2θ) in the range of 25.6°-26.0°".

Likewise, throughout the present specification, "having an absorption peak at a wavenumber of 616±1 cm$^{-1}$" means "having an absorption peak at a wavenumber in the range of 615-617 cm$^{-1}$", and "having an absorption peak at a wavenumber of 802±1 cm$^{-1}$" means "having an absorption peak at a wavenumber in the range of 801-803 cm$^{-1}$".

Throughout the present specification, "having a peak at a chemical shift of approximately 134.7 ppm" means "having a peak substantially equivalent to a chemical shift of 134.7 ppm, when a $^{13}$C solid state NMR spectrum is measured under ordinary measuring conditions". Also, "having a peak at a chemical shift of approximately 126.3 ppm" as used throughout the present specification means "having a peak substantially equivalent to a chemical shift of 126.3 ppm, when a $^{13}$C solid state NMR spectrum is measured under ordinary measuring conditions".

The crystals (Form A) of the invention may be obtained, for example, by recrystallization of the crystals (Form C) of the invention from a mixed solvent of ethanol and water.

Process for Preparing a Crystalline Form (Form C) (Crystallization Method)

The crystals (Form C) of the invention may be stably produced on an industrial scale by producing the compound (5b) according to Example 1 of Patent document 1 or Production Example 3A of the present specification, and then crystallizing the compound (5b) from a specific solvent. The compound (5b) used for crystallization may be in any form. That is, it may be a hydrate or anhydrate, amorphous or crystalline (including combinations of multiple crystal forms) compound, or a mixture thereof.

The solvent used for crystallization is a simple solvent selected from the group consisting of n-propyl alcohol, isopropyl alcohol, n-butyl alcohol, s-butyl alcohol, t-butyl alcohol and water, or a mixed solvent thereof. A mixed solvent is preferably a mixture of two different solvents selected from the group listed above. Preferred solvents are a simple solvent of isopropyl alcohol or s-butyl alcohol, a mixed solvent of s-butyl alcohol and water or a mixed solvent of isopropyl alcohol and water, more preferred solvents are a mixed solvent of s-butyl alcohol and water or a mixed solvent of isopropyl alcohol and water, and even more preferred solvent is a mixed solvent of s-butyl alcohol and water.

The mixing ratio (volume ratio) when using a mixed solvent of s-butyl alcohol and water is preferably 3:1-5:1, more preferably 3.9:1-4.1:1 and even more preferably 4:1.

The mixing ratio (volume ratio) when using a mixed solvent of isopropyl alcohol and water is preferably 5:1-100:1, more preferably 9:1-100:1, even more preferably 9.9:1-10.1:1 and most preferably 10:1.

The amount of solvent used may be appropriately selected between the minimum amount in which the compound (5b) will dissolve by heating and the maximum amount at which the yield of the crystals is not significantly reduced, and it is preferably a 3-40 fold amount (v/w), more preferably a 10-20 fold amount (v/w), even more preferably a 15-17 fold amount (v/w) and most preferably a 15.7-16.3 fold amount (v/w), in terms of the volume ratio with respect to the weight of the compound (5b).

The temperature for dissolution of the compound (5b) may be appropriately selected as the temperature at which the compound (5b) will dissolve in the solvent, but it is preferably from 75° C. to heating reflux temperature. The cooling during crystallization is preferably carried out while suitably adjusting the cooling rate in consideration of the effect on quality and grade of the crystals, and gradual cooling (cooling at a rate of 40° C./hr or slower) is preferred. More preferably, the cooling rate is 5-20° C./hr and even more preferably it is about 10° C./hr. The final crystallization temperature may be appropriately selected in view of the yield and quality of the crystals, but it is preferably from room temperature to 0° C., more preferably 9-5° C. and even more preferably 6.5-7.5° C.

The precipitated crystals may be separated by an ordinary filtration procedure, washed with an appropriate solvent if necessary, and then dried to afford the desired crystals. The solvent used for washing of the crystals is the same as the crystallization solvent, and is preferably s-butyl alcohol.

When the crystals separated by the filtration procedure consist (mainly) of anhydrate crystals (Form C), drying may be accomplished by merely standing in air, but in the case of mass production this is not efficient, and therefore drying by heating is preferred. The drying temperature may be appropriately selected depending on the production volume, but it is preferably 40-130° C., more preferably 65-75° C. and even more preferably 70° C. The drying time may be appropriately selected as a time up to which the residual solvent falls below a prescribed volume, depending on the production volume, drying apparatus and drying temperature. The drying may be carried out under an airflow or under reduced pressure, but it is preferably carried out under reduced pressure. The degree of pressure reduction may be appropriately selected depending on the production volume, drying apparatus and drying temperature.

Process for Preparing a Crystalline Form (Form C) (Thermal Transition Method)

The crystals (Form C) may also be produced by thermal transition of the compound (5b). The compound (5b) used for thermal transition may be in any form. That is, it may be a hydrate or anhydrate, amorphous or crystalline (including combinations of multiple crystal forms) compound, or a mixture thereof. A particularly preferred form is hydrate crystals of the compound (5b), or a mixture of anhydrate crystals of the compound (5b) and hydrate crystals of the compound (5b). The mixture may be, for example, a mixture obtained by rapid cooling during recrystallization of the compound (5b) (see Examples 2B and 1D of the present specification).

Heat drying of the compound (5b) with a heat drying apparatus can afford a crystalline form (Form C) of N-(3-cyano-4-methyl-1H-indol-7-yl)-3-cyanobenzenesulfonamide anhydrate.

The heating temperature may be appropriately selected depending on the production volume, but is preferably 80-130° C., more preferably 119-121° C. and even more preferably 120° C. The drying time may be appropriately selected as a time up to which the residual solvent falls below a prescribed volume, depending on the production volume, drying apparatus and drying temperature, but it is preferably between 10 minutes and 12 hours and more preferably between 30 minutes and 3 hours. The drying may be carried out under an airflow or under reduced pressure, but it is preferably carried out under reduced pressure. The degree of pressure reduction may be appropriately selected depending on the production volume, drying apparatus and drying temperature.

The compound (5b) may also be suspended in water, stirred while heating and then filtered to afford the crystals (Form C). The amount of water used is not particularly restricted, but is preferably a 5-30 fold amount (v/w), more preferably an 18-22 fold amount (v/w) and even more preferably a 20-fold amount (v/w) with respect to the hydrate-containing crystals to be suspended. The temperature for heated stirring may be 60-90° C., preferably 75-85° C. and more preferably 80° C. The time for heated stirring may be 1-24 hours, preferably 3-18 hours and more preferably 16-18 hours.

The obtained anhydrate crystals may be subjected to additional drying with the same method and conditions as the drying method and conditions described for the crystallization method.

The crystals (Form C) obtained by the process described above consist of a single crystal form which is stable, does not readily convert to other crystal forms or an amorphous form and has satisfactory physical properties such as lack of hygroscopicity, and they are therefore suitable for formulation.

Pharmaceutical Composition Comprising Crystals of the Invention

The use of the compound (5b) as an antitumor agent is disclosed in detail in Patent document 1, and the crystals of the invention may be used in a similar fashion as the active ingredient of an antitumor agent. The entirety of the disclosure of Patent document 1 is incorporated by reference into the disclosure of the present specification. Moreover, the crystals (Form C) of the invention have satisfactory stability and physical properties and are hence the most suitable form for use of the compound (5b) as the active ingredient of an antitumor agent.

The crystals of the invention may be formulated by an ordinary method into tablets, powder, fine powder, granules, coated tablets, capsules, syrup, lozenges, an inhalant, suppository, injection, ointment, eye ointment, eye drop, nose drop, ear drop, pap, lotion or the like. For formulation there may be employed commonly used excipients, binders, lubricants, coloring agents, taste correctives and, if necessary, stabilizers, emulsifiers, absorption accelerators, surfactants, pH adjustors, antiseptics, antioxidants and the like, while other components ordinarily used as starting materials for drug formulation may also be added according to common procedures.

As examples of such components there may be mentioned animal or vegetable oils such as soybean oil, beef tallow and synthetic glycerides; hydrocarbons such as liquid paraffin, squalene and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerin fatty acid ester, polyoxyethylenesorbitan fatty acid ester, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropyl alcohol; polyhydric alcohols such as glycerin, propylene glycol, dipropylene glycol and sorbitol; sugars such as glucose and sucrose; inorganic powders such as silicic anhydride, magnesium aluminum silicate and aluminum silicate, purified water, and the like.

As examples of excipients there may be mentioned lactose, corn starch, white soft sugar, glucose, mannitol, sorbit, crystalline cellulose, silicon dioxide and the like, as examples of binders there may be mentioned polyvinyl alcohol, polyvinyl ether, methylcellulose, ethylcellulose, gum Arabic, tragacanth gum, gelatin, shellac, hydroxypropylmethylcellulose, hydroxypropylcellulose, polyvinylpyrrolidone, polypropylene glycol-polyoxyethylene block polymer, meglumine and the like, as examples of disintegrators there may be mentioned starch, agar, gelatin powder, crystalline cellulose, calcium carbonate, sodium hydrogencarbonate, calcium citrate, dextrin, pectin, carboxymethylcellulose calcium and the like, as examples of lubricants there may be mentioned magnesium stearate, talc, polyethylene glycol, silica, hydrogenated vegetable oils and the like, as examples of coloring agents there may be mentioned those approved for addition to pharmaceuticals, and as examples of taste correctives there may be mentioned cocoa powder, menthol, aromatic powder, peppermint oil, camphor, cinnamon powder and the like.

For production of an oral preparation, the compound of the invention or its pharmacologically acceptable salt may be combined with an excipient and, if necessary, a binder, disintegrator, lubricant, coloring agent, taste corrective or the like and then made into a powder, fine powder, granules, tablets, coated tablets or capsules.

Also, there is no restriction against sugar-coating and, if necessary, other appropriate coating of the tablets or granules.

For production of a liquid preparation such as a syrup or pharmaceutical preparation for injection, the compound of the invention or its pharmacologically acceptable salt may be combined with a pH adjustor, solubilizer, isotonizing agent or the like, and if necessary, with a dissolving aid, stabilizers or the like, and formulated by an ordinary method.

The method of producing an external preparation is not particularly restricted, and may be according to an ordinary method. Specifically, as base materials for pharmaceutical preparation there may be used various materials ordinarily employed for pharmaceuticals, quasi drugs, cosmetics and the like. As examples of specific base materials to be used there may be mentioned materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, and if necessary there may also be added pH adjustors, antioxidants, chelating agents, antiseptic/mildew resistant agents, coloring agents, aromatics and the like, although base materials for an external preparation of the invention are not limited to these. If necessary there may also be included components such as circulation promoters, bactericidal agents, antiflash agents, cell activators, vitamins, amino acids, humectants, keratolytic agents and the like. The amounts of such base materials are the amounts which give concentrations indicated for production of ordinary external preparations.

The form of administration of the crystals of the invention is not particularly restricted, and may be oral administration or parenteral administration by an ordinarily employed method. For example, the crystals may be administered after formulation into tablets, powder, granules, capsules, syrup, lozenges, an inhalant, suppository, injection, ointment, eye ointment, eye drop, nose drop, ear drop, pap, lotion or the like. The dosage of a pharmaceutical according to the invention may be appropriately selected depending on patient age, gender, body weight, severity of symptoms, particular type of condition, and on the type of dosage form or salt.

The following are examples of pharmaceutical formulations comprising a crystalline form (Form C) of N-(3-cyano-4-methyl-1H-indol-7-yl)-3-cyanobenzenesulfonamide anhydrate (compound (5b), crystals Form C), to be used for treatment or prevention in humans.

Whole formulation for 100 mg preparation (content per tablet)

TABLE 1

| Ingredient | Purpose of use | Content (mg) |
| --- | --- | --- |
| Compound (5b), crystals Form C | principal agent | 100.0 |
| Mannitol | excipient | 123.8 |
| Corn starch | excipient | 36.0 |
| Low substituted hydroxypropylcellulose | disintegrator | 48.0 |
| Hydroxypropylcellulose | binder | 9.6 |
| Magnesium stearate | lubricant | 2.6 |
| Hydroxypropylmethylcellulose | coating agent | 5.7 |
| Macrogol | coating agent | 1.2 |
| Talc | coating agent | 2.6 |
| Titanium oxide | coating agent | 0.45 |
| Yellow iron oxide | coloring agent | 0.05 |
| Total | | 330 mg |

Whole formulation for 50 mg preparation (content per tablet)

TABLE 2

| Ingredient | Purpose of use | Content (mg) |
| --- | --- | --- |
| Compound (5b), crystals Form C | principal agent | 50.0 |
| Mannitol | excipient | 61.9 |
| Corn starch | excipient | 18.0 |
| Low substituted hydroxypropylcellulose | disintegrator | 24.0 |
| Hydroxypropylcellulose | binder | 4.8 |
| Magnesium stearate | lubricant | 1.3 |
| Hydroxypropylmethylcellulose | coating agent | 3.4 |
| Macrogol | coating agent | 0.7 |
| Talc | coating agent | 1.6 |
| Titanium oxide | coating agent | 0.27 |
| Yellow iron oxide | coloring agent | 0.03 |
| Total | | 166 mg |

Whole formulation for 10 mg preparation (content per tablet)

TABLE 3

| Ingredient | Purpose of use | Content (mg) |
| --- | --- | --- |
| Compound (5b), crystals Form C | principal agent | 10.0 |
| Mannitol | excipient | 89.9 |
| Corn starch | excipient | 38.0 |
| Low substituted hydroxypropylcellulose | disintegrator | 16.0 |
| Hydroxypropylcellulose | binder | 4.8 |
| Magnesium stearate | lubricant | 1.3 |
| Hydroxypropylmethylcellulose | coating agent | 3.4 |
| Macrogol | coating agent | 0.7 |
| Talc | coating agent | 1.6 |
| Titanium oxide | coating agent | 0.27 |
| Yellow iron oxide | coloring agent | 0.03 |
| Total | | 166 mg |

Whole formulation for 2 mg preparation (content per tablet)

TABLE 4

| Ingredient | Purpose of use | Content (mg) |
| --- | --- | --- |
| Compound (5b), crystals Form C | principal agent | 2.0 |
| Mannitol | excipient | 95.9 |
| Corn starch | excipient | 40.0 |
| Low substituted hydroxypropylcellulose | disintegrator | 16.0 |
| Hydroxypropylcellulose | binder | 4.8 |
| Magnesium stearate | lubricant | 1.3 |
| Hydroxypropylmethylcellulose | coating agent | 3.4 |
| Macrogol | coating agent | 0.7 |
| Talc | coating agent | 1.6 |
| Titanium oxide | coating agent | 0.27 |
| Yellow iron oxide | coloring agent | 0.03 |
| Total | | 166 mg |

The pharmaceutical preparations having the formulations listed above may be obtained by ordinary pharmaceutical protocols.

EXAMPLES

The present invention will now be explained in greater detail and specifically by the following examples, with the understanding that the invention is in no way limited to the examples.

Example 1A

Production of 3-cyano-4-methyl-7-nitro-1H-indole

[Chemical Formula 1]

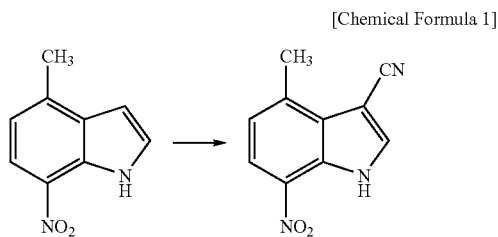

To 740 mL of dimethylformamide was added 235 mL (2.52 mol) of phosphorous oxychloride at 0° C., followed by stirring at 0° C. for 0.5 hour. To the reaction mixture was then added a solution of 370 g (2.10 mol) of 4-methyl-7-nitro-1H-indole (WO00/50395) in dimethylformamide (1110 mL) at 0° C., followed by heating and stirring at 60° C. for 2 hours.

To the reaction mixture was then added dropwise a solution of 292 g (4.20 mol) of hydroxylamine hydrochloride in dimethylformamide (1850 mL) with keeping the internal temperature below 80° C., followed by heating and stirring at 60° C. for 40 minutes. After adding 11.1 L of ice water to the reaction mixture while cooling in an ice bath, the mixture was further stirred overnight. The precipitated crystals were collected by filtration and washed with water. The crystals were suspended in 11.1 L of water, 1N solution of sodium hydroxide was added to the suspension for adjustment to pH 7, and then the crystals were collected by filtration and washed with water to give 412 g of the title compound (yield: 97.6%).

HPLC analysis confirmed that the obtained compound was identical to the 3-cyano-4-methyl-7-nitro-1H-indole described in WO00/50395.

(HPLC Conditions)

Mobile phase: $CH_3CN/H_2O/70\% HClO_4=500/500/1$ (v/v/v)

Flow rate: 1.0 mL/min

Detection: UV (254 nm)

Column: YMC-Pack Pro C18 250×4.6 mm

Example 2A

Production of 7-amino-3-cyano-4-methyl-1H-indole

[Chemical Formula 2]

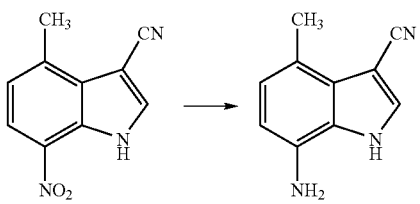

After suspending 400 g (1.99 mol) of the 3-cyano-4-methyl-7-nitro-1H-indole obtained in Example 1A in a mixture of 6 L of ethyl acetate and 6 L of methanol, the suspension was subjected to hydrogenation in the presence of 40 g of 10% palladium-carbon at ordinary temperature, 4 atmospheres. After removing the catalyst by filtration, the filtrate was treated with activated carbon and concentrated to give crude crystals. The crude crystals were dissolved in 6 L of 1,2-dimethoxyethane at an external temperature of 60° C., and then 12 L of water was added dropwise. Upon confirming precipitation of crystals, the mixture was stirred for 1.5 hours while cooling in an ice bath and filtered, and the crystals were washed twice with water (1 L). The crystals were air-dried at 50° C. for 16 hours to give 289 g of the title compound (yield: 84.8%).

HPLC analysis confirmed that the obtained compound was identical to the 7-amino-3-cyano-4-methyl-1H-indole described in WO00/50395.

(HPLC Conditions)

Mobile phase: $CH_3CN/H_2O/70\% HClO_4=400/600/1$ (v/v/v)

Flow rate: 1.0 mL/min

Detection: UV (282 nm)

Column: YMC-Pack Pro C18 250×4.6 mm

Example 3A

Production of N-(3-cyano-4-methyl-1H-indol-7-yl)-3-cyanobenzenesulfonamide (anhydrate crystals (Form C))

[Chemical Formula 3]

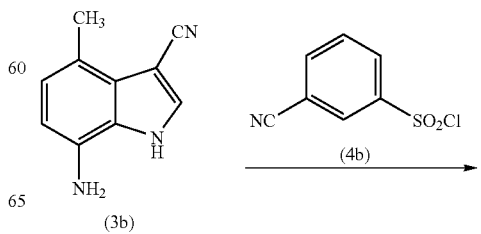

-continued

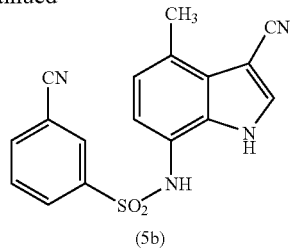

(5b)

To a suspension of 5.0 g (29 mmol) of the 7-amino-3-cyano-4-methyl-1H-indole obtained in Example 2A and 6.48 g (32 mmol) of 3-cyanobenzenesulfonyl chloride [CAS No. 56542-67-7] in 150 mL of methyl acetate, were added 75 mL of water and 2.83 mL (35 mmol) of pyridine, followed by stirring for 2 hours and 40 minutes. After adding 0.73 mL (9 mmol) of concentrated hydrochloric acid to the reaction mixture, liquid-liquid separation was performed and the organic layer was washed with a mixture of 75 mL of water and 17.5 mL of ethanol. Activated carbon was added to the organic layer and the mixture was stirred at 45-50° C. for 30 minutes, and then filtered and concentrated. To thus obtained crude crystals were added 96 mL of 2-butanol and 24 mL of water for dissolution at 75° C., and the solution was cooled to 7° C. at approximately 10° C./hr and stirred overnight. The precipitated crystals were collected by filtration and washed twice with 10 mL of 2-butanol to give 8.17 g (wet weight) of crystals of the title compound. The crystals were dried under reduced pressure at 70° C. for 2 hours to give 7.54 g of crystals of the title compound.

HPLC analysis confirmed that the obtained compound was identical to the N-(3-cyano-4-methyl-1H-indol-7-yl)-3-cyanobenzenesulfonamide described in WO00/50395.

(HPLC Conditions)

Mobile phase: $CH_3CN/H_2O/70\%\ HClO_4 = 500/500/1$ (v/v/v)

Flow rate: 1.0 mL/min

Detection: UV (282 nm)

Column: YMC-Pack Pro C18 250×4.6 mm

A powder X-ray diffraction pattern for the obtained crystals is shown in FIG. 1, and the diffraction angle (2θ) peak and peak intensity are shown in Table 5.

TABLE 5

| PEAK No. | 2 θ | INTERPLANAR SPACING | INTENSITY | HALF WIDTH | I/Io |
|---|---|---|---|---|---|
| 1 | 11.420 | 7.74203 | 2122 | 0.210 | 55 |
| 2 | 13.040 | 6.78363 | 913 | 0.210 | 24 |
| 3 | 14.380 | 6.15437 | 778 | 0.300 | 20 |
| 4 | 15.200 | 5.82415 | 717 | 0.210 | 19 |
| 5 | 15.540 | 5.69748 | 220 | 0.210 | 6 |
| 6 | 16.380 | 5.40714 | 1013 | 0.210 | 26 |
| 7 | 17.000 | 5.21131 | 960 | 0.210 | 25 |
| 8 | 19.080 | 4.64763 | 3925 | 0.240 | 100 |
| 9 | 19.440 | 4.56237 | 505 | 0.150 | 13 |
| 10 | 19.780 | 4.48471 | 1512 | 0.240 | 39 |
| 11 | 20.360 | 4.35824 | 470 | 0.210 | 12 |
| 12 | 20.900 | 4.24684 | 543 | 0.210 | 14 |
| 13 | 22.500 | 3.94833 | 1295 | 0.150 | 33 |
| 14 | 22.620 | 3.92765 | 1437 | 0.270 | 37 |
| 15 | 23.160 | 3.83728 | 295 | 0.120 | 8 |
| 16 | 23.950 | 3.71094 | 920 | 0.330 | 24 |
| 17 | 24.400 | 3.64501 | 890 | 0.180 | 23 |
| 18 | 24.520 | 3.62744 | 952 | 0.150 | 25 |
| 19 | 24.980 | 3.56168 | 917 | 0.240 | 24 |
| 20 | 25.560 | 3.48216 | 693 | 0.210 | 18 |
| 21 | 26.260 | 3.39090 | 1230 | 0.270 | 32 |
| 22 | 26.760 | 3.32867 | 823 | 0.240 | 21 |
| 23 | 28.840 | 3.09315 | 1277 | 0.210 | 33 |
| 24 | 29.620 | 3.01345 | 270 | 0.180 | 7 |

Example 1B

Production of N-(3-cyano-4-methyl-1H-indol-7-yl)-3-cyanobenzenesulfonamide (mixture consisting mainly of anhydrate crystals (Form B))

Crystals of the title compound were synthesized using the same reactions conditions and recrystallization conditions as for the N-(3-cyano-4-methyl-1H-indol-7-yl)-3-cyanobenzenesulfonamide described in WO00/50359.

To a solution of 7-amino-3-cyano-4-methyl-1H-indole (10 g, 58.4 mmol) in tetrahydrofuran (200 ml) were added pyridine (20 ml) and 3-cyanobenzenesulfonyl chloride (12.5 g), followed by stirring at room temperature for 3.5 hours. After further adding 2N hydrochloric acid (100 ml), extraction was performed with ethyl acetate. The organic layer was washed with water (twice) and brine in that order, dried over anhydrous magnesium sulfate, and then concentrated under reduced pressure. The residue was purified by silica gel column chromatography (hexane:ethyl acetate=2:1-3:2). A mixed solvent of ethanol-hexane (1:2) was added thereto, and after sonication, the precipitate was collected by filtration and washed with a mixed solvent of ethanol-hexane (1:3). The mixture was dried overnight under reduced pressure to give the title compound (9.33 g, 27.7 mmol, 47% yield).

$^1$H-NMR spectrum (DMSO-$d_6$) δ (ppm): 2.58 (3H, s), 6.52 (1H, d, J=7.6 Hz), 6.80 (1H, d, J=7.6 Hz), 7.74 (1H, m), 7.92 (1H, d, J=8.0 Hz), 8.12 (2H, m), 8.19 (1H, d, J=3.2 Hz), 10.13 (1H, s), 12.03 (1H, s).

Figure 2:
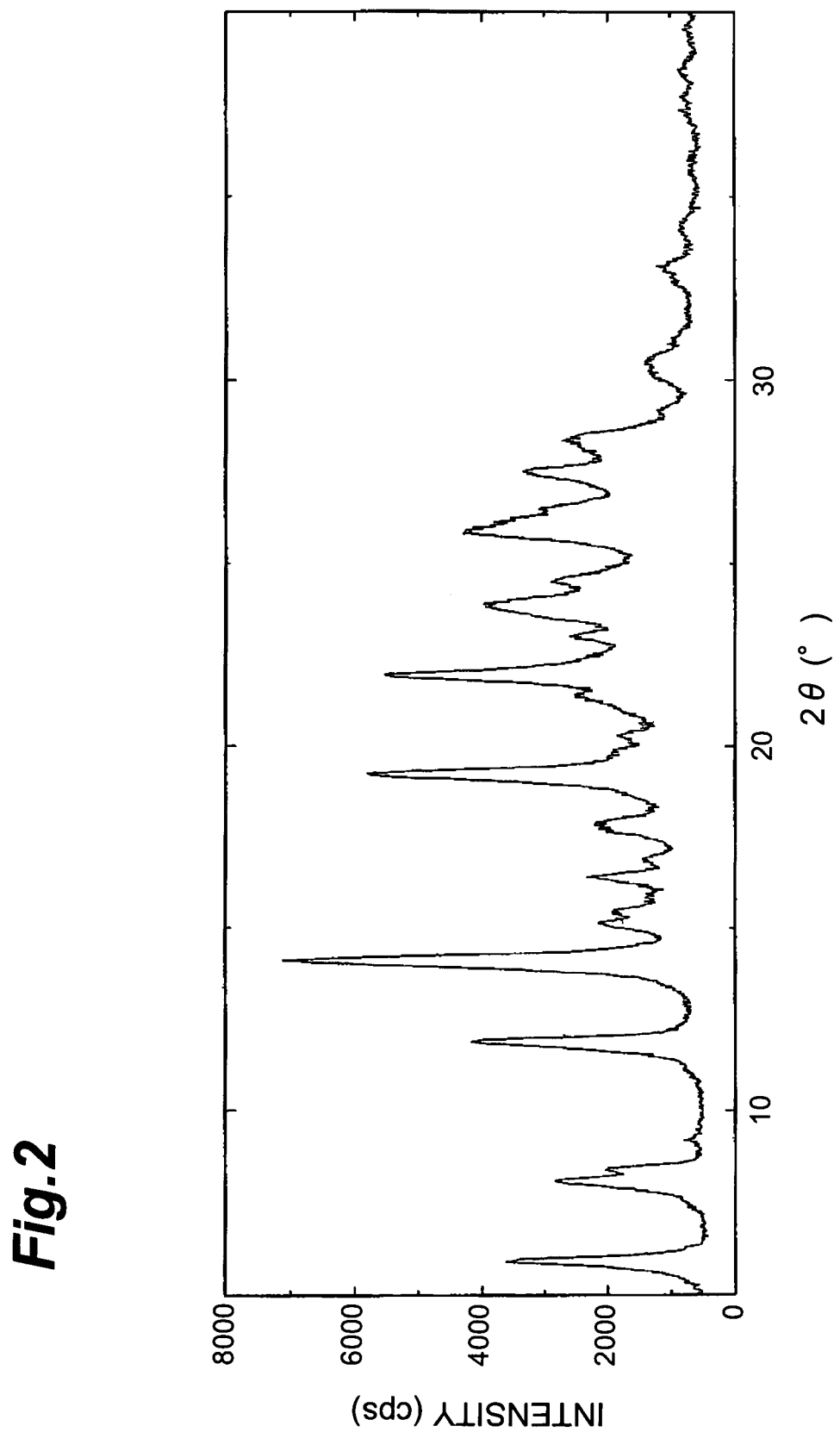
FIG. 2 is a drawing representing a powder X-ray diffraction pattern of the crystals obtained in Example 1B.

A powder X-ray diffraction pattern for the obtained crystals is shown in FIG. 2, and the diffraction angle (2θ) peak and peak intensity are shown in Table 6.

TABLE 6

| PEAK No. | 2 θ | HALF WIDTH | d-VALUE | INTENSITY | RELATIVE INTENSITY |
|---|---|---|---|---|---|
| 1 | 5.960 | 0.235 | 14.8167 | 3492 | 49 |
| 2 | 8.100 | 0.212 | 10.9063 | 2820 | 40 |
| 3 | 8.440 | 0.188 | 10.4677 | 1968 | 28 |
| 4 | 11.920 | 0.259 | 7.4184 | 4067 | 57 |
| 5 | 14.120 | 0.282 | 6.2671 | 7103 | 100 |
| 6 | 15.120 | 0.259 | 5.8548 | 2142 | 30 |
| 7 | 16.400 | 0.165 | 5.4006 | 2330 | 33 |
| 8 | 17.660 | 0.141 | 5.0180 | 1905 | 27 |
| 9 | 17.960 | 0.212 | 4.9349 | 1998 | 28 |
| 10 | 19.240 | 0.306 | 4.6093 | 5707 | 80 |
| 11 | 21.380 | 0.235 | 4.1526 | 2443 | 34 |
| 12 | 21.940 | 0.282 | 4.0478 | 5502 | 77 |
| 13 | 23.020 | 0.212 | 3.8603 | 2602 | 37 |
| 14 | 23.580 | 0.165 | 3.7699 | 3172 | 45 |
| 15 | 23.900 | 0.400 | 3.7201 | 3958 | 56 |
| 16 | 24.540 | 0.282 | 3.6245 | 2812 | 40 |
| 17 | 25.840 | 0.165 | 3.4451 | 4302 | 61 |
| 18 | 26.520 | 0.212 | 3.3582 | 3045 | 43 |

TABLE 6-continued

| PEAK No. | 2 θ | HALF WIDTH | d-VALUE | INTENSITY | RELATIVE INTENSITY |
|---|---|---|---|---|---|
| 19 | 27.540 | 0.376 | 3.2361 | 3265 | 46 |
| 20 | 28.380 | 0.118 | 3.1422 | 2655 | 37 |
| 21 | 28.520 | 0.188 | 3.1271 | 2435 | 34 |

It was attempted to produce identical crystals by the same process as Example 1B, but the powder X-ray diffraction pattern did not match. In other words, the crystals obtained in Example 1B were presumably not of a single crystal form but were a mixture of multiple crystal forms. Moreover, it is believed that a single crystal form cannot by the process of Example 1B.

Example 2B

Production of N-(3-cyano-4-methyl-1H-indol-7-yl)-3-cyanobenzenesulfonamide (anhydrate crystals (Form C)) (Alternative method 1)

After suspending N-(3-cyano-4-methyl-1H-indol-7-yl)-3-cyanobenzenesulfonamide (mixture consisting mainly of hydrate crystals) (1.00 g) obtained by the same process as Example 1B in isopropyl alcohol (5.0 ml), the mixture was heated to reflux. Isopropyl alcohol (16.0 ml) was gradually added thereto, for complete dissolution of the crystals. The solution was heated to reflux for 30 minutes, and then heating of the oil bath was stopped and stirring was performed for 12 hours. The precipitated crystals were collected by filtration, and the crystals were washed with isopropyl alcohol (2 ml×3) and suction-dried at room temperature for 10 minutes. Thus obtained crystals were dried at 50° C. for 13.5 hours, and then pounded in a mortar. This was dried at 50° C. for 13 hours to give a mixture (744 mg) of hydrate crystals and anhydrate crystals (Form C) of N-(3-cyano-4-methyl-1H-indol-7-yl)-3-cyanobenzenesulfonamide, as light yellow to light brown crystals.

A 200 mg portion thereof was dried at 120° C. for 30 minutes to give crystals of N-(3-cyano-4-methyl-1H-indol-7-yl)-3-cyanobenzenesulfonamide (194 mg).

When a powder X-ray diffraction pattern of the obtained crystals was measured, it matched the diffraction pattern of the crystals obtained in Example 1C, confirming that the obtained crystals were identical crystals to the crystals obtained in Example 1C (anhydrate crystals (Form C)).

Example 1C

Production of N-(3-cyano-4-methyl-1H-indol-7-yl)-3-cyanobenzenesulfonamide (anhydrate crystals (Form C)) (Alternative method 2)

After suspending 2.50 kg (14.6 mol) of 7-amino-3-cyano-4-methyl-1H-indole and 3.24 kg (16.06 mol) of 3-cyanobenzenesulfonyl chloride [CAS No. 56542-67-7] in 25 L of methyl acetate, 87.5 L of methyl acetate and 37.5 L of water were added thereto. Next, 1.39 kg (17.52 mol) of pyridine was added dropwise and the mixture was stirred for 2 hours.

After adding 0.36 L (4.38 mol) of concentrated hydrochloric acid to the reaction mixture, it was subjected to liquid-liquid separation and the organic layer was washed with a mixture of 37.5 L of water and 8.8 L of ethanol. After adding activated carbon to the organic layer and stirring at 50° C. for 30 minutes, the mixture was filtered and concentrated. To this was added 30 L of isopropyl alcohol, and after re-concentration, 91 L of isopropyl alcohol and 9.1 L of water were added and the mixture was heated to 70° C. Dissolution was confirmed after 2 hours, and then clarifying filtration was performed and 11.4 L of isopropyl alcohol and 1.1 L of water were added. The solution was slowly cooled to 7° C. at 10° C./hr (with introduction of seed crystals at 64° C.), and after stirring overnight at 7° C., the crystals were collected by filtration. The crystals were dried at 70° C. under reduced pressure to give 3.6 kg of the title compound as a white crystalline powder (yield: 73%).

The moisture content of the obtained white crystalline powder was measured by the Karl Fischer method to be 0.1%, confirming that the obtained crystals were anhydrate crystals. HPLC analysis also confirmed that the obtained crystals were N-(3-cyano-4-methyl-1H-indol-7-yl)-3-cyanobenzenesulfonamide.

(HPLC Conditions)

Mobile phase: $CH_3CN/H_2O/70\% \ HClO_4=500/500/1$ (v/v/v)

Flow rate: 1.0 ml/min

Detection: UV (282 nm)

Column: YMC-Pack Pro C18 250×4.6 mm

Column temperature: 25° C.

Retention time: 8.3 min

Figure 3:
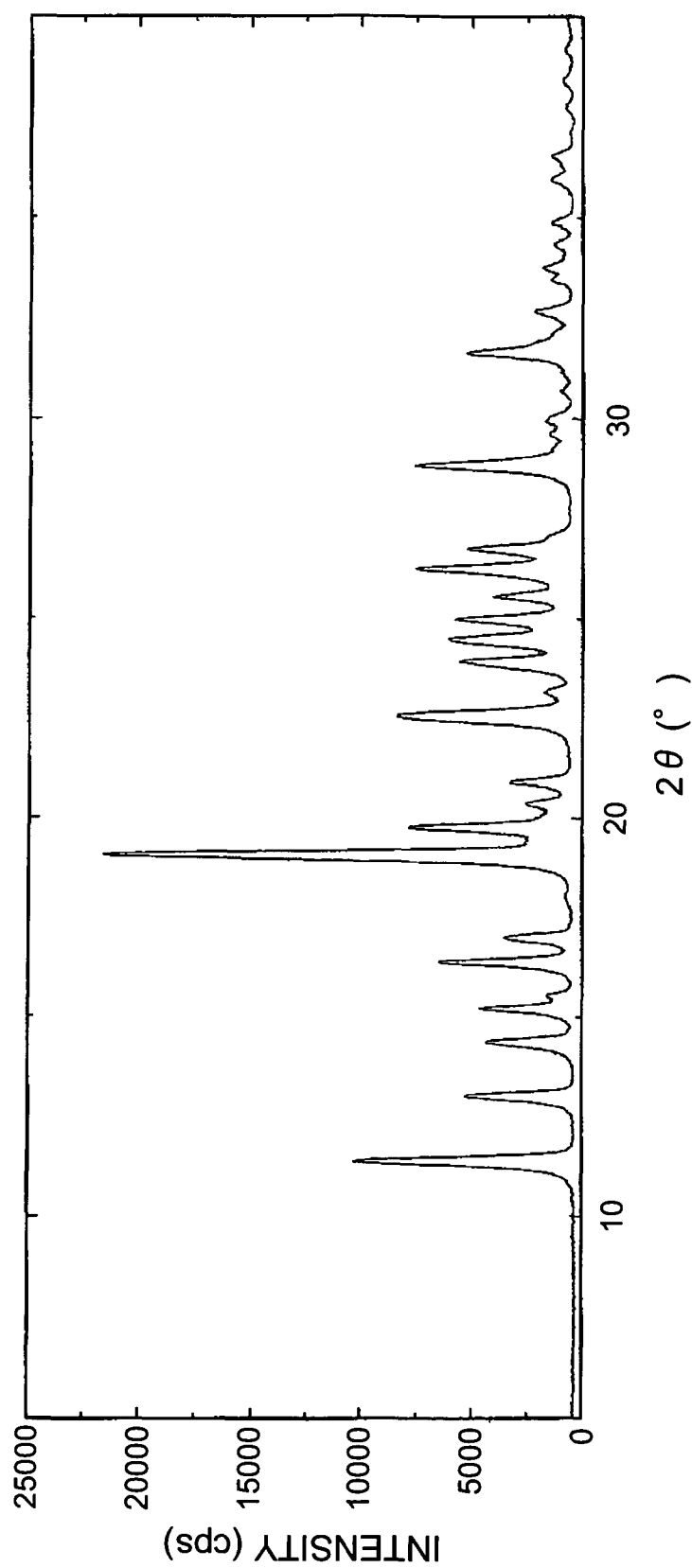
FIG. 3 is a drawing representing a powder X-ray diffraction pattern of the crystals obtained in Example 1C.

A powder X-ray diffraction pattern for the obtained crystals is shown in FIG. 3, and the diffraction angle (2θ) peak and peak intensity are shown in Table 7.

TABLE 7

| 2 theta (degree) | Relative Intensity |
|---|---|
| 11.4 | 47 |
| 13.0 | 24 |
| 14.4 | 20 |
| 15.2 | 21 |
| 16.4 | 30 |
| 17.0 | 16 |
| 19.1 | 100 |
| 19.8 | 36 |
| 20.4 | 12 |
| 20.9 | 15 |
| 22.6 | 37 |
| 24.0 | 25 |
| 24.5 | 28 |
| 25.0 | 27 |
| 25.6 | 19 |
| 26.3 | 35 |
| 26.8 | 23 |
| 28.8 | 35 |
| 31.6 | 24 |
| 32.7 | 10 |

Figure 5:
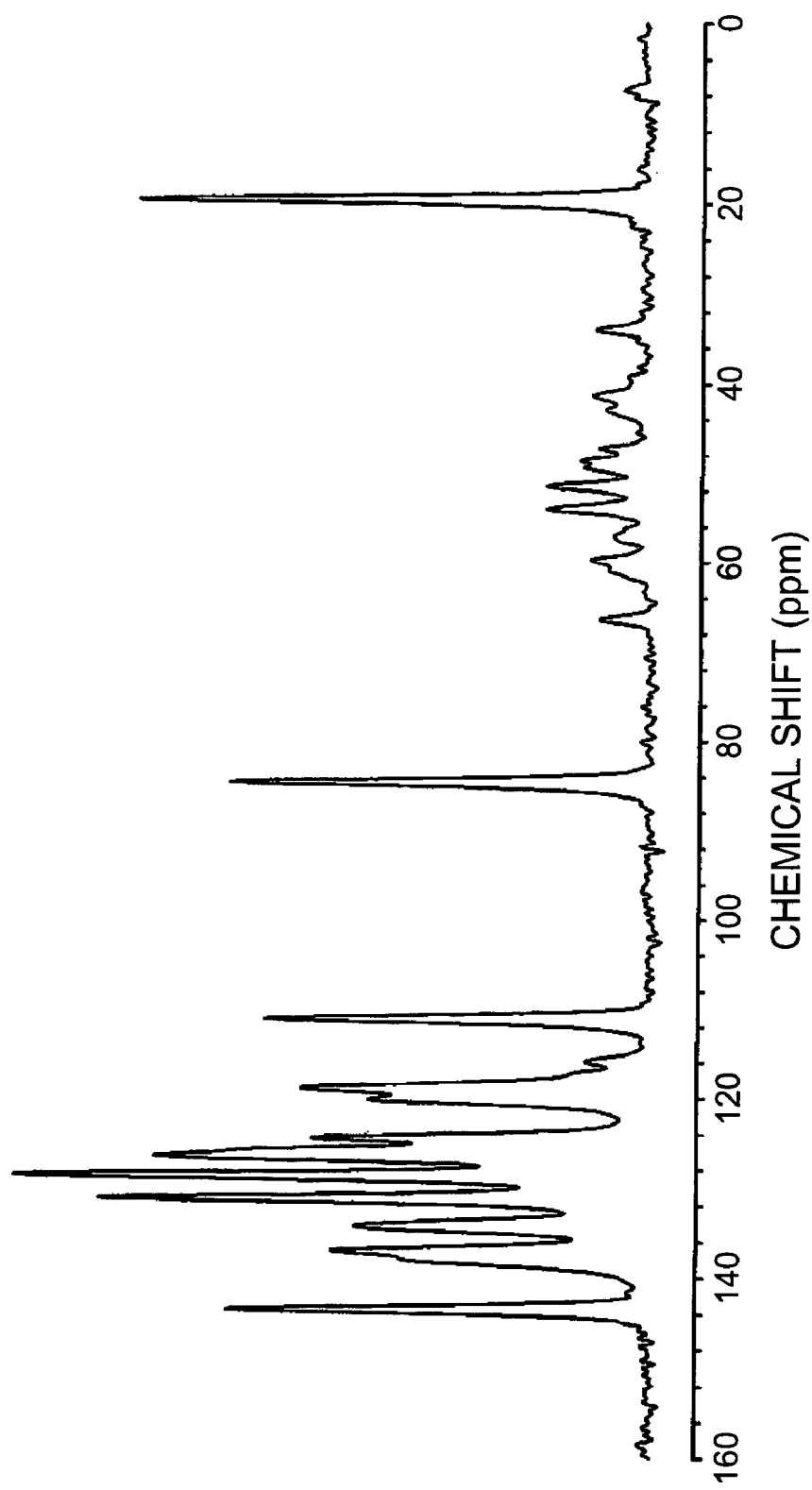
FIG. 5 is a drawing representing a $^{13}$C solid state NMR spectrum of the crystals obtained in Example 1C.

A $^{13}C$ solid-state NMR spectrum for the obtained crystals is shown in FIG. 5, and the chemical shifts are listed in Table 8.

TABLE 8

| Chemical Shift (ppm) |
|---|
| 143.4 |
| 137.7 |
| 136.9 |
| 134.2 |
| 131.1 |
| 128.5 |
| 126.4 |

TABLE 8-continued

| Chemical Shift (ppm) |
| --- |
| 125.8 |
| 124.3 |
| 120.0 |
| 118.8 |
| 115.8 |
| 111.0 |
| 84.5 |
| 19.4 |

Figure 7:
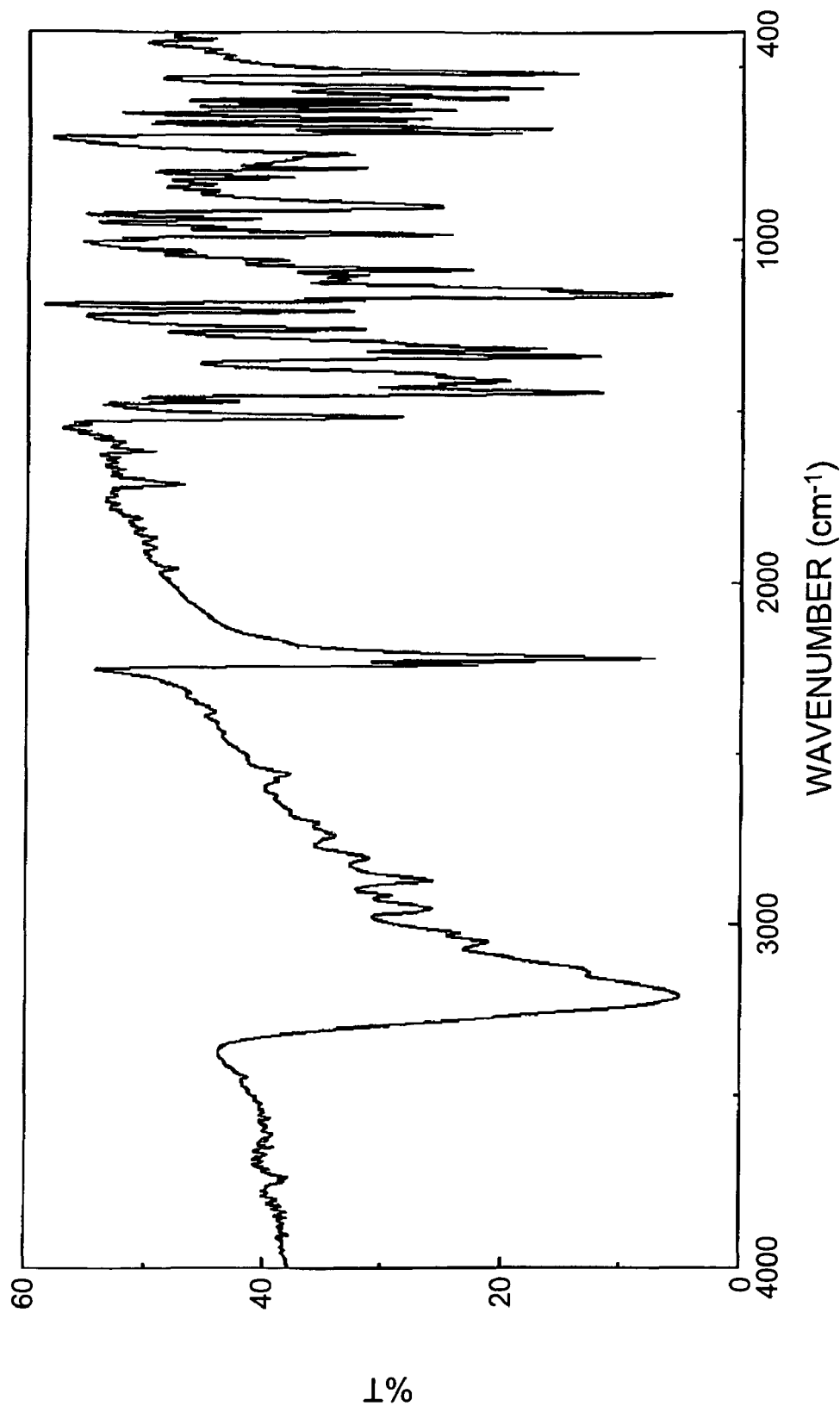
FIG. 7 is a drawing representing an infrared absorption spectrum (KBr) of the crystals obtained in Example 1C.

An infrared spectrum (KBr) for the obtained crystals is shown in FIG. 7, and the wavenumbers (cm$^{-1}$) and transmittances (% T) of the absorption peak are shown in Table 9.

TABLE 9

| Wavenumber (cm − 1) | % T |
| --- | --- |
| 3212 | 5 |
| 2954 | 26 |
| 2872 | 26 |
| 2242 | 22 |
| 2223 | 7 |
| 1715 | 47 |
| 1617 | 49 |
| 1519 | 29 |
| 1472 | 42 |
| 1443 | 12 |
| 1410 | 20 |
| 1337 | 12 |
| 1316 | 17 |
| 1260 | 32 |
| 1207 | 33 |
| 1178 | 32 |
| 1158 | 6 |
| 1102 | 32 |
| 1087 | 23 |
| 1060 | 38 |
| 984 | 25 |
| 939 | 41 |
| 905 | 25 |
| 839 | 45 |
| 819 | 38 |
| 795 | 32 |
| 754 | 33 |
| 690 | 19 |
| 676 | 16 |
| 652 | 26 |
| 625 | 24 |
| 607 | 28 |
| 588 | 20 |
| 559 | 17 |
| 518 | 14 |
| 420 | 45 |

Example 1D

Production of N-(3-cyano-4-methyl-1H-indol-7-yl)-3-cyanobenzenesulfonamide (hydrate crystals (Form A))

N-(3-Cyano-4-methyl-1H-indol-7-yl)-3-cyanobenzenesulfonamide (31.8 g) was dissolved in isopropyl alcohol (954 ml) and water (9.5 ml) at an external temperature of 80° C. Anhydrate seed crystals (95.4 mg) were added, and rapid ice-cooling was carried out. After stirring for 30 minutes, the crystals were collected by filtration, washed twice with isopropyl alcohol (60 ml), and dried at 19° C. for 3.5 hours under reduced pressure to give white crystals of the title compound (28.1 g). A powder X-ray diffraction pattern of the obtained crystals was measured, and it matched the diffraction pattern of the crystals obtained in Example 1F, confirming that the crystals obtained in this example were of the same type as the crystals obtained in Example 1F.

Example 2D

Production of N-(3-cyano-4-methyl-1H-indol-7-yl)-3-cyanobenzenesulfonamide (anhydrate crystals (Form C)) (Alternative method 3)

After suspending the N-(3-cyano-4-methyl-1H-indol-7-yl)-3-cyanobenzenesulfonamide (5 g) obtained in Example 1D in water (100 ml), the mixture was heated and stirred at 80° C. for 17 hours. It was then allowed to cool down to room temperature, and then the crystals were collected by filtration, washed with water (20 ml) and dried under reduced pressure at 70° C. for 22 hours to give crystals of the title compound (4.20 g) (yield: 97.7%).

A powder X-ray diffraction pattern of the obtained crystals was measured, and it matched the diffraction pattern of the crystals obtained in Example 1C, confirming that the obtained crystals were identical crystals to the crystals obtained in Example 1C (anhydrate crystals (Form C)).

Example 1E

Production of N-(3-cyano-4-methyl-1H-indol-7-yl)-3-cyanobenzenesulfonamide (anhydrate crystals (Form B))

After dissolving N-(3-cyano-4-methyl-1H-indol-7-yl)-3-cyanobenzenesulfonamide (anhydrate crystals (Form C), 1.0 g) in a mixed solution of dehydrated ethanol (36 mL) and water (6 mL) in a water bath at 70° C., the solution was allowed to stand in ice water. The precipitated crystals were filtered, and the obtained crystals were dried at 200° C. to give N-(3-cyano-4-methyl-1H-indol-7-yl)-3-cyanobenzenesulfonamide (anhydrate crystals (Form B)).

Figure 9:
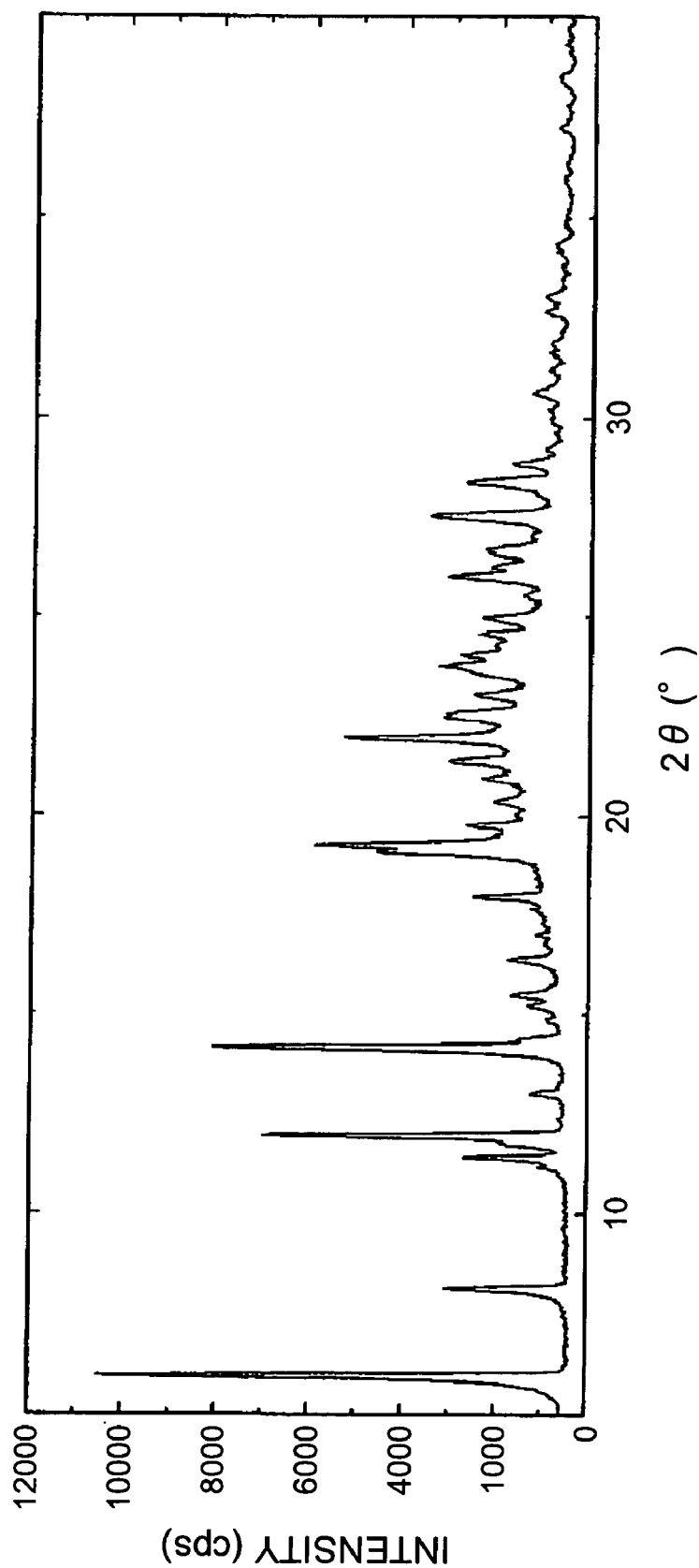
FIG. 9 is a drawing representing a powder X-ray diffraction pattern of the crystals obtained in Example 1E.

A powder X-ray diffraction pattern for the obtained crystals is shown in FIG. 9.

Example 1F

Production of N-(3-cyano-4-methyl-1H-indol-7-yl)-3-cyanobenzenesulfonamide (hydrate crystals (Form A))

After dissolving N-(3-cyano-4-methyl-1H-indol-7-yl)-3-cyanobenzenesulfonamide (anhydrate crystals (Form C), 1.0 g) in a mixed solution of dehydrated ethanol (36 mL) and water (6 mL) in a water bath at 70° C., the solution was allowed to stand in an ice water bath. The precipitated crystals were filtered to give N-(3-cyano-4-methyl-1H-indol-7-yl)-3-cyanobenzenesulfonamide (hydrate crystals (Form A)).

Figure 4:
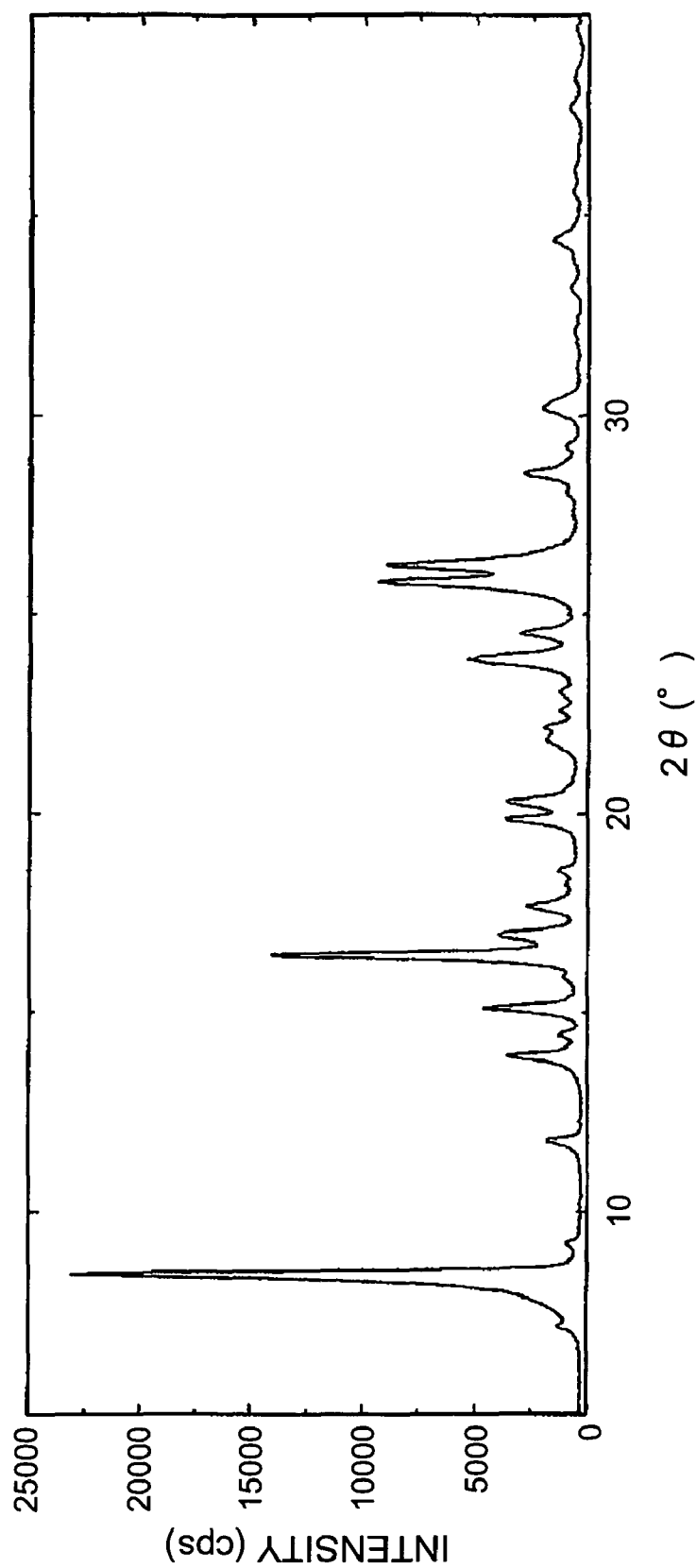
FIG. 4 is a drawing representing a powder X-ray diffraction pattern of the crystals obtained in Example 1F.

A powder X-ray diffraction pattern for the obtained crystals is shown in FIG. 4, and the diffraction angle (2θ) peak and peak intensity are shown in Table 10.

TABLE 10

| 2 theta (degree) | Relative Intensity |
| --- | --- |
| 8.5 | 100 |
| 11.8 | 8 |
| 13.9 | 14 |
| 15.1 | 20 |
| 16.5 | 61 |
| 17.0 | 17 |

TABLE 10-continued

| 2 theta (degree) | Relative Intensity |
|---|---|
| 17.7 | 11 |
| 19.9 | 16 |
| 20.3 | 16 |
| 21.8 | 8 |
| 22.2 | 8 |
| 23.9 | 23 |
| 24.5 | 13 |
| 25.8 | 41 |
| 26.3 | 39 |
| 28.6 | 13 |
| 30.2 | 9 |
| 34.4 | 7 |

Figure 6:
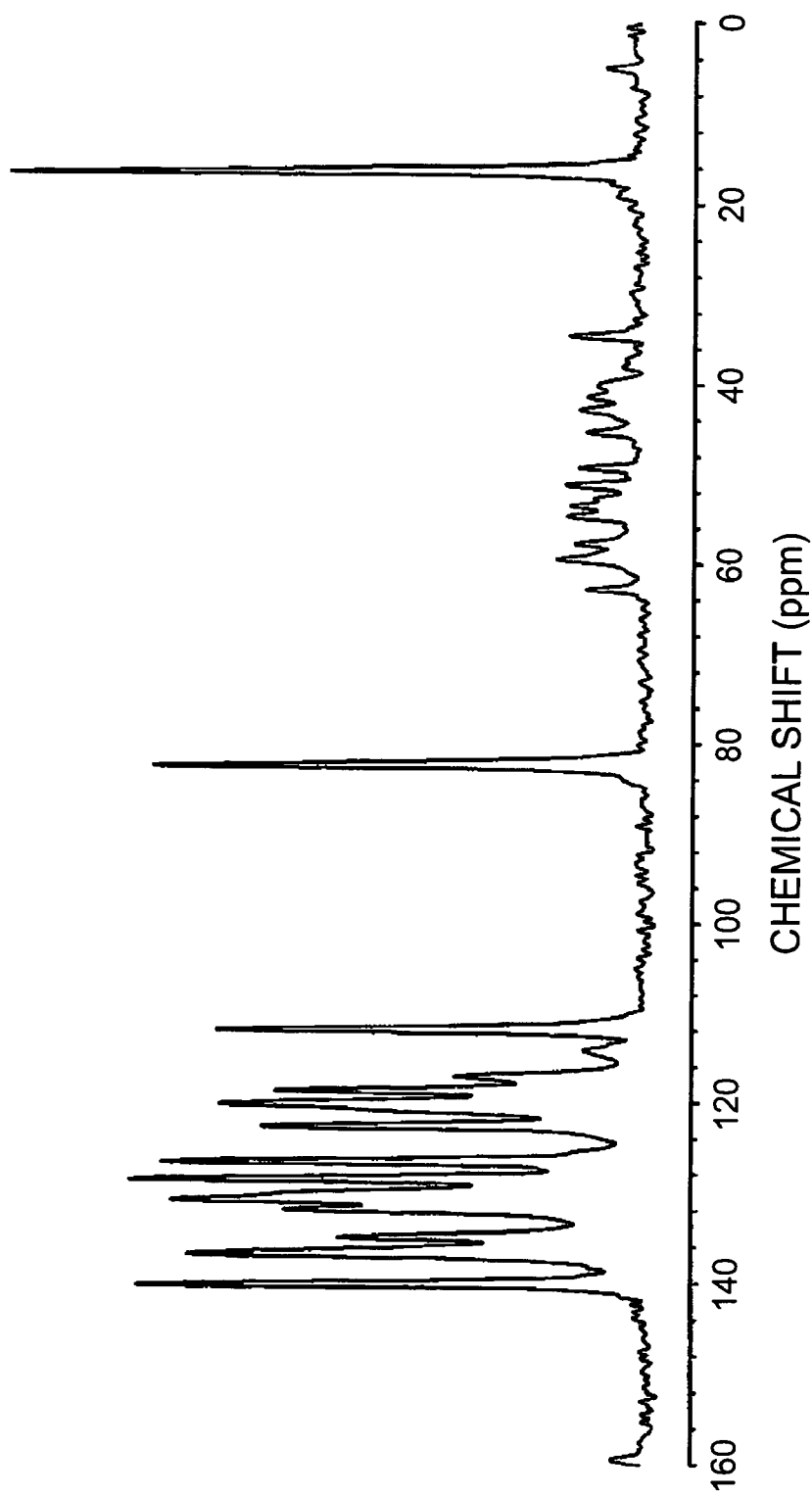
FIG. 6 is a drawing representing a $^{13}$C solid state NMR spectrum of the crystals obtained in Example 1F.

A $^{13}$C solid-state NMR spectrum for the obtained crystals is shown in FIG. 6, and the chemical shifts are listed in Table 11.

TABLE 11

| Chemical Shift (ppm) |
|---|
| 139.9 |
| 136.5 |
| 134.7 |
| 131.7 |
| 130.5 |
| 129.9 |
| 128.2 |
| 126.3 |
| 122.4 |
| 119.9 |
| 118.4 |
| 116.9 |
| 114.1 |
| 111.7 |
| 82.1 |
| 16.1 |

Figure 8:
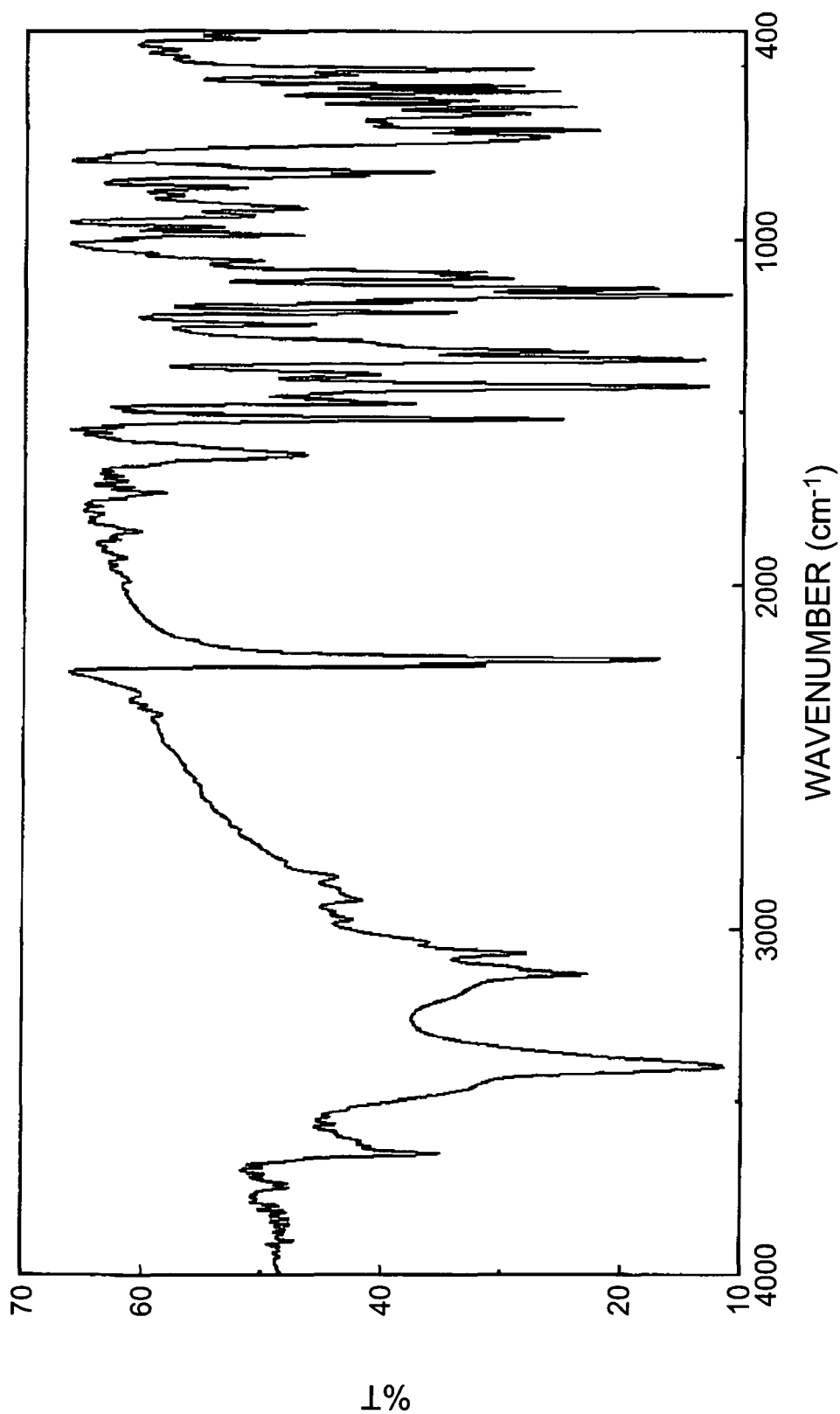
FIG. 8 is a drawing representing an infrared absorption spectrum (KBr) of the crystals obtained in Example 1F.

An infrared spectrum (KBr) for the obtained crystals is shown in FIG. 8, and the wavenumbers (cm$^{-1}$) and transmittances (% T) of the absorption peak are shown in Table 12.

TABLE 12

| Wavenumber (cm − 1) | % T |
|---|---|
| 3749 | 48 |
| 3650 | 35 |
| 3400 | 12 |
| 3131 | 23 |
| 3071 | 28 |
| 2916 | 42 |
| 2233 | 32 |
| 2217 | 17 |
| 1846 | 60 |
| 1734 | 58 |
| 1621 | 47 |
| 1517 | 25 |
| 1472 | 37 |
| 1422 | 13 |
| 1389 | 40 |
| 1347 | 13 |
| 1320 | 23 |
| 1244 | 46 |
| 1206 | 34 |
| 1179 | 38 |
| 1160 | 11 |
| 1139 | 17 |
| 1108 | 29 |
| 1091 | 32 |
| 1060 | 50 |
| 982 | 47 |
| 964 | 54 |

TABLE 12-continued

| Wavenumber (cm − 1) | % T |
|---|---|
| 928 | 51 |
| 907 | 47 |
| 850 | 52 |
| 813 | 42 |
| 802 | 36 |
| 702 | 26 |
| 682 | 22 |
| 635 | 28 |
| 616 | 24 |
| 597 | 32 |
| 572 | 26 |
| 556 | 29 |
| 526 | 42 |
| 508 | 28 |
| 420 | 51 |

(Powder X-ray Diffraction Measurement)

Powder X-ray diffraction measurements for the crystals obtained in each of the examples was carried out under the following measuring conditions.

[Measuring Conditions A]

X-rays: CuKα rays

Tube voltage: 40 kV

Tube current: 20 mA

Divergence slit: 1°

Receiving slit: 0.15 mm

Scattering slit: 1°

Scan speed: 2°/min

[Measuring Conditions B]

X-rays: CuKα rays

Tube voltage: 40 kV

Tube current: 200 mA

Divergence slit: ½°

Receiving slit: 0.3 mm

Scattering slit: ½°

Scan speed: 2°/min

The crystals obtained in Example 3A were measured under measuring conditions A above, and the crystals obtained in Examples 1B, 1C, 1E and 1F were measured under measuring conditions B above.

($^{13}$C Solid State NMR Spectroscopy)

$^{13}$C solid state NMR spectrum measurements of the crystals obtained in Examples 1C and 1F were conducted under the following conditions.

Measuring temperature: Room temperature (~22° C.)

Standard substance: Silicone rubber (internal standard: 1.56 ppm)

Measuring nucleus: $^{13}$C (75.188829 MHz)

Pulse repeat time: 70 sec (Form A: Example 1F), 150 sec (Form C: Example 1C)

Pulse mode: CP/MAS measurement (VACPX-pm)

(Infrared Absorption Spectroscopy (KBr))

Infrared spectrum measurements of the crystals obtained in Examples 1C and 1F were conducted by the potassium bromide disk method.

Test Example 1

Purity of Crystals Obtained in Example 1B

The impurity content in the crystals obtained in Example 1B was measured by HPLC.

(HPLC Conditions)

Column: ODS column (inner diameter=4.6 mm, column length=250 mm, particle size=5 μm)

Column temperature: 30° C.

Detection wavenumber: 282 nm

Flow rate: 1.0 mL/min

Mobile Phase:

Solution A: $CH_3CN/H_2O/70\%\ HClO_4=100/900/1$ (v/v/v)

Solution B: $CH_3CN/H_2O/70\%\ HClO_4=900/100/1$ (v/v/v)

The gradient program is shown in Table 13.

TABLE 13

| Time (min) | Solution B (%) |
|---|---|
| Initial | 35 |
| 40 | 100 |
| 50 | 100 |

(Impurity Content Calculation Method)

All of the peaks and peak areas were calculated from the chromatogram, and the impurity amount for each peak (except for the peak of N-(3-cyano-4-methyl-1H-indol-7-yl)-3-cyanobenzenesulfonamide) was calculated according to the following formula.

Individual impurity content(%)=(individual impurity peak area)/(total of all peak areas)×100

Peaks with impurity contents of 0.05% or greater were recorded as impurity peaks, and their total was recorded as the impurity content of the crystals.

Impurity content(%)=Total of individual impurity contents (%)

The results of HPLC analysis demonstrated that the crystals obtained in Example 1B contained 2.17% impurities.

Test Example 2

Solid Stability Against Light

The crystals obtained in Example 1C, Example 1E and Example 1F were stored for 1 month and 3 months at 25° C./1000 Lx (LT-120D3J Light Stability Tester by Nagano Science, Japan), and then the impurity contents were measured by HPLC.

(HPLC Conditions)

HPLC was conducted under the same conditions as in Test Example 1, except that elution was performed with the gradient program shown in Table 14.

TABLE 14

| Time (min) | Solution B (%) |
|---|---|
| Initial | 35 |
| 25 | 35 |
| 40 | 100 |
| 50 | 100 |

The impurity content of the crystals was determined by the same method as described for Test Example 1. The impurity contents of the crystals obtained in different examples before and after storage are listed in Table 15. As shown in Table 15, no change in impurity content before and after storage was seen for Example 1F and Example 1C, but the impurity content increased before and after storage for Example 1E. That is, the crystals obtained in Examples 1F and 1C (Form A and Form C) clearly had higher stability against light.

TABLE 15

| Storage conditions | Impurity content (%) | | |
|---|---|---|---|
| | Example 1F | Example 1E | Example 1C |
| Before storage | 0.42 | 0.50 | 0.51 |
| 25° C./1000 Lx/1 month | 0.41 | 0.83 | 0.51 |
| 25° C./1000 Lx/3 months | 0.51 | 4.44 | 0.51 |

These results demonstrated that highly pure crystals can be obtained by the process for preparing a crystalline form of N-(3-cyano-4-methyl-1H-indol-7-yl)-3-cyanobenzenesulfonamide (Form C) according to the invention, and that the obtained crystals (Form C) have high stability against light and properties suitable for pharmaceutical formulation.

INDUSTRIAL APPLICABILITY

The present invention provides crystalline N-(3-cyano-4-methyl-1H-indol-7-yl)-3-cyanobenzenesulfonamide having a single crystal form and excellent stability against light, as well as a process for preparing the same. The crystals may be used as the active ingredient of a pharmaceutical composition, and especially are suitable for use as the active ingredient of an angiogenesis inhibitor, antitumor agent, pancreatic cancer therapeutic agent, colorectal cancer therapeutic agent, gastric cancer therapeutic agent, breast cancer therapeutic agent, prostate cancer therapeutic agent, lung cancer therapeutic agent, ovarian cancer therapeutic agent, cancer metastasis inhibitor, diabetic retinopathy therapeutic agent, rheumatoid arthritis therapeutic agent or angioma therapeutic agent.

The invention claimed is:

1. A crystalline form of N-(3-cyano-4-methyl-1H-indol-7-yl)-3-cyanobenzenesulfonamide having the X-ray diffraction pattern as depicted in FIG. 3.

* * * * *